(12) United States Patent
Schreck

(10) Patent No.: US 6,920,349 B2
(45) Date of Patent: Jul. 19, 2005

(54) SYSTEM AND METHOD FOR PREDICTING THE ONSET OF CARDIAC PATHOLOGY USING FRACTAL ANALYSIS

(76) Inventor: David M. Schreck, 80 Division Ave., Summit, NJ (US) 07901

( * ) Notice: Subject to any disclaimer, the term of this patent is extended or adjusted under 35 U.S.C. 154(b) by 554 days.

(21) Appl. No.: 10/187,662

(22) Filed: Jul. 1, 2002

(65) Prior Publication Data

US 2004/0002661 A1 Jan. 1, 2004

(51) Int. Cl.$^7$ .............................................. A61B 5/0402
(52) U.S. Cl. ....................................... 600/512; 600/509
(58) Field of Search ................................ 128/923–925; 600/508–510, 512–513, 515–518

(56) References Cited

U.S. PATENT DOCUMENTS

| | | |
|---|---|---|
| 4,850,370 A | 7/1989 | Dower |
| 5,058,598 A | 10/1991 | Nicklas et al. |
| 5,318,037 A | 6/1994 | Evans et al. |
| 5,377,687 A | 1/1995 | Evans et al. |
| 5,471,991 A | 12/1995 | Shinnar |
| 5,694,942 A | 12/1997 | Escalona |
| 6,144,877 A | 11/2000 | DePetrillo |

OTHER PUBLICATIONS

David M. Schreck, U.S. Appl. No. 10/150,719 entitled "Method and Apparatus for Synthesizing Leads of an Electrocardiogram," filed May 17, 2002,.

M. J. Katz, "Fractals and the Analysis of Waveforms," from "Comput. Biol. Med." vol. 18, No. 3, pp. 145–156, 1988 (Pergamon Press).

E. Frank, "An Accurate, Clinically Practical System for Spatial Vectorcardiography," Circulation, vol. XIII, May 1956, pp. 737–749.

F. C. Moon, Chaotic and Fractal Dynamics, An Introduction for Applied Scientists and Engineers, Wiley–Interscience Publication, John Wiley & Sons, Inc., pp. 325–341.

*Primary Examiner*—Kennedy Schaetzle
*Assistant Examiner*—Kristen Mullen
(74) *Attorney, Agent, or Firm*—Greenberg Traurig

(57) ABSTRACT

The onset of cardiac pathology can be predicted by first acquiring a plurality of lead values as a function of time for set of electrocardiogram leads and defining a spatial curve from the lead values for at least three leads. A fractal index for the spatial curve is calculated as a function of time and the time rate of change of the fractal index is monitored. A negative time rate of change is indicative of normal cardiac activity, while a positive time rate of change is indicative of pathological cardiac activity.

18 Claims, 11 Drawing Sheets

| ST | I | II | III | aVR | aVL | aVF | V1 | V2 | V3 | V4 | V5 | V6 | RAY D | ARC L | IF/THEN DD | PERIM LSUM | | X | FRAC D FD -Y |
|---|---|---|---|---|---|---|---|---|---|---|---|---|---|---|---|---|---|---|---|
| 1 | 0 | 0 | 0 | 0 | 0 | 0 | 0 | 0 | 0 | 0 | 0 | 0 | 0 | 0 | 0 | 0 | | 1 | 0 |
| 2 | -3 | -3 | 0 | 2.61 | -1.3 | -1.3 | 8 | 5 | 2 | 0 | -1 | -3 | 11.45505 | 11.45505 | 11.45505 | 11.45505 | | 2 | 0 |
| 3 | -3 | -1 | 2 | 1.74 | -2.2 | 0.44 | 19 | 20 | 11 | 4 | -1 | -3 | 30.49504 | 21.34342 | 30.49504 | 32.79846 | | 3 | 1.070987 |
| 4 | -3 | 3 | 6 | 0 | -3.9 | 3.92 | 27 | 35 | 25 | 14 | 4 | -2 | 53.66241 | 25.71314 | 53.66241 | 58.51161 | | 4 | 1.066559 |
| 5 | 8 | 22 | 14 | -13.1 | -2.6 | 15.7 | 27 | 52 | 52 | 44 | 30 | 14 | 101.6629 | 60.87652 | 101.6629 | 119.3881 | | 5 | 1.110937 |
| 6 | 28 | 52 | 24 | -34.8 | 1.74 | 33.1 | 27 | 77 | 100 | 98 | 75 | 44 | 200.4845 | 104.7127 | 200.4845 | 224.1008 | | 6 | 1.066269 |
| 7 | 64 | 92 | 28 | -67.9 | 15.7 | 52.2 | 11 | 112 | 162 | 172 | 136 | 86 | 339.5645 | 144.399 | 339.5645 | 368.4998 | | 7 | 1.043868 |
| 8 | 105 | 125 | 20 | -100 | 37 | 63.1 | -15 | 140 | 221 | 245 | 197 | 128 | 475.6991 | 142.1189 | 475.6991 | 510.6187 | | 8 | 1.035267 |
| 9 | 142 | 152 | 10 | -128 | 57.4 | 70.5 | -54 | 140 | 250 | 294 | 243 | 164 | 570.4243 | 107.7996 | 570.4243 | 618.4183 | | 9 | 1.03817 |
| 10 | 162 | 171 | 9 | -145 | 66.6 | 78.3 | -106 | 99 | 239 | 308 | 264 | 186 | 603.6749 | 82.59279 | 603.6749 | 701.0111 | | 10 | 1.069429 |
| 11 | 151 | 164 | 13 | -137 | 60 | 77 | -154 | 17 | 168 | 251 | 235 | 176 | 528.7766 | 136.2005 | 603.6749 | 837.2116 | | 11 | 1.157926 |
| 12 | 121 | 123 | 2 | -106 | 51.8 | 54.4 | -185 | -84 | 46 | 130 | 146 | 134 | 382.4199 | 233.6832 | 603.6749 | 1070.895 | | 12 | 1.299846 |
| 13 | 88 | 64 | -24 | -66.1 | 48.7 | 17.4 | -179 | -144 | -64 | 13 | 61 | 86 | 296.0123 | 217.205 | 603.6749 | 1288.1 | | 13 | 1.419403 |
| 14 | 46 | 20 | -26 | -28.7 | 31.3 | -2.6 | -148 | -168 | -142 | -74 | -1 | 44 | 287.5918 | 163.1094 | 603.6749 | 1451.209 | | 14 | 1.497813 |
| 15 | 25 | 5 | -20 | -13.1 | 19.6 | -6.5 | -107 | -136 | -127 | -76 | -17 | 27 | 233.4825 | 67.67206 | 603.6749 | 1518.881 | | 15 | 1.516812 |
| 16 | 17 | 2 | -15 | -8.27 | 13.9 | -5.7 | -70 | -84 | -78 | -47 | -13 | 18 | 146.813 | 86.98064 | 603.6749 | 1605.862 | | 16 | 1.545299 |
| 17 | 17 | 4 | -13 | -9.14 | 13.1 | -3.9 | -45 | -48 | -43 | -24 | -2 | 16 | 88.07428 | 61.74578 | 603.6749 | 1667.608 | | 17 | 1.559192 |
| 18 | 18 | 15 | -3 | -14.4 | 9.14 | 5.22 | -27 | -22 | -18 | -4 | 10 | 20 | 54.1088 | 50.32916 | 603.6749 | 1717.937 | | 18 | 1.566998 |
| 19 | 18 | 21 | 3 | -17 | 6.53 | 10.4 | -17 | -10 | -5 | 5 | 13 | 20 | 47.13152 | 24.81678 | 603.6749 | 1742.754 | | 19 | 1.562656 |
| 20 | 15 | 21 | 6 | -15.7 | 3.92 | 11.7 | -8 | 1 | 3 | 12 | 16 | 18 | 43.57187 | 18.87374 | 603.6749 | 1761.627 | | 20 | 1.556407 |
| 21 | 13 | 17 | 4 | -13.1 | 3.92 | 9.14 | -1 | 8 | 8 | 12 | 14 | 14 | 37.52436 | 13.43965 | 603.6749 | 1775.067 | | 21 | 1.548615 |
| 22 | 11 | 14 | 3 | -10.9 | 3.48 | 7.4 | 1 | 12 | 8 | 12 | 13 | 11 | 33.97149 | 7.207458 | 603.6749 | 1782.275 | | 22 | 1.539032 |
| 23 | 10 | 13 | 3 | -10 | 3.05 | 6.96 | 3 | 12 | 8 | 10 | 10 | 9 | 30.55836 | 4.912774 | 603.6749 | 1787.187 | | 23 | 1.529411 |
| 24 | 8 | 12 | 4 | -8.7 | 1.74 | 6.96 | 4 | 14 | 9 | 10 | 10 | 9 | 30.41643 | 3.925054 | 603.6749 | 1791.112 | | 24 | 1.520238 |
| 25 | 8 | 12 | 4 | -8.7 | 1.74 | 6.96 | 6 | 16 | 11 | 11 | 10 | 9 | 32.65209 | 3.605551 | 603.6749 | 1794.718 | | 25 | 1.5117 |
| 26 | 9 | 12 | 3 | -9.14 | 2.61 | 6.53 | 8 | 18 | 13 | 12 | 11 | 9 | 35.63476 | 4.139487 | 603.6749 | 1798.857 | | 26 | 1.504043 |
| 27 | 9 | 10 | 1 | -8.27 | 3.48 | 4.79 | 8 | 19 | 13 | 13 | 11 | 9 | 35.35982 | 3.813319 | 603.6749 | 1802.671 | | 27 | 1.49685 |
| 28 | 8 | 10 | 2 | -7.83 | 2.61 | 5.22 | 9 | 20 | 14 | 13 | 11 | 8 | 35.97735 | 2.671208 | 603.6749 | 1805.342 | | 28 | 1.489763 |
| 29 | 8 | 10 | 2 | -7.83 | 2.61 | 5.22 | 9 | 20 | 15 | 13 | 11 | 8 | 36.37814 | 1 | 603.6749 | 1806.342 | | 29 | 1.482559 |
| 30 | 8 | 11 | 3 | -8.27 | 2.18 | 6.09 | 10 | 22 | 16 | 13 | 12 | 8 | 39.00165 | 3.183606 | 603.6749 | 1809.526 | | 30 | 1.47659 |
| 31 | 8 | 11 | 3 | -8.27 | 2.18 | 6.09 | 11 | 23 | 16 | 14 | 12 | 9 | 40.38724 | 2 | 603.6749 | 1811.526 | | 31 | 1.470596 |
| 32 | 8 | 11 | 3 | -8.27 | 2.18 | 6.09 | 11 | 24 | 17 | 14 | 12 | 9 | 41.36579 | 1.414214 | 603.6749 | 1812.94 | | 32 | 1.464767 |
| 33 | 8 | 12 | 4 | -8.7 | 1.74 | 6.96 | 11 | 26 | 18 | 16 | 13 | 9 | 44.68959 | 3.759701 | 603.6749 | 1816.699 | | 33 | 1.460062 |
| 34 | 8 | 12 | 4 | -8.7 | 1.74 | 6.96 | 12 | 26 | 19 | 16 | 13 | 10 | 45.35592 | 1.414214 | 603.6749 | 1818.114 | | 34 | 1.454864 |
| 35 | 8 | 12 | 4 | -8.7 | 1.74 | 6.96 | 13 | 27 | 20 | 17 | 13 | 10 | 46.98041 | 2 | 603.6749 | 1820.114 | | 35 | 1.450139 |
| 36 | 8 | 12 | 4 | -8.7 | 1.74 | 6.96 | 13 | 27 | 20 | 17 | 13 | 10 | 46.98041 | 0 | 603.6749 | 1820.114 | | 36 | 1.445025 |
| 37 | 8 | 13 | 5 | -8.7 | 1.74 | 7.83 | 13 | 27 | 20 | 17 | 15 | 11 | 48.34729 | 2.852253 | 603.6749 | 1822.966 | | 37 | 1.441062 |
| 38 | 9 | 13 | 4 | -9.57 | 2.18 | 7.4 | 14 | 28 | 22 | 19 | 15 | 11 | 50.8724 | 3.624272 | 603.6749 | 1826.59 | | 38 | 1.437545 |
| 39 | 9 | 14 | 5 | -10 | 1.74 | 8.27 | 14 | 29 | 23 | 19 | 15 | 11 | 52.40647 | 2.266131 | 603.6749 | 1828.856 | | 39 | 1.433794 |
| 40 | 9 | 15 | 6 | -10.4 | 1.31 | 9.14 | 14 | 29 | 24 | 19 | 15 | 12 | 53.65766 | 2.266131 | 603.6749 | 1831.122 | | 40 | 1.430225 |
| 41 | 9 | 15 | 6 | -10.4 | 1.31 | 9.14 | 14 | 30 | 25 | 20 | 15 | 12 | 56.01915 | 3 | 603.6749 | 1834.122 | | 41 | 1.427042 |
| 42 | 10 | 16 | 6 | -11.3 | 1.74 | 9.57 | 15 | 31 | 26 | 22 | 16 | 12 | 57.97007 | 3.022474 | 603.6749 | 1837.145 | | 42 | 1.424017 |
| 43 | 10 | 16 | 6 | -11.3 | 1.74 | 9.57 | 15 | 32 | 28 | 23 | 16 | 12 | 59.80409 | 2.44949 | 603.6749 | 1839.594 | | 43 | 1.420964 |
| 44 | 10 | 16 | 6 | -11.3 | 1.74 | 9.57 | 14 | 33 | 29 | 23 | 17 | 12 | 60.84841 | 2 | 603.6749 | 1841.594 | | 44 | 1.417916 |
| 45 | 10 | 18 | 8 | -12.2 | 0.87 | 11.3 | 14 | 33 | 30 | 23 | 17 | 13 | 62.74572 | 3.813319 | 603.6749 | 1845.408 | | 45 | 1.415515 |
| 46 | 10 | 19 | 9 | -12.6 | 0.44 | 12.2 | 15 | 33 | 30 | 24 | 19 | 13 | 64.57306 | 3.022474 | 603.6749 | 1848.43 | | 46 | 1.412999 |

Fig. 17

SYSTEM AND METHOD FOR PREDICTING THE ONSET OF CARDIAC PATHOLOGY USING FRACTAL ANALYSIS

FIELD OF THE INVENTION

This invention is directed to the prediction of acute cardiac activity from the fractal analysis of spatial loops generated from the synthesized leads of an electrocardiogram ("ECG") derived from three measured leads belonging to the set of routinely used leads, including the standard 12-lead ECG.

BACKGROUND OF THE INVENTION

The ECG is a record of the electrical activity of the heart that is a commonly used diagnostic screening test in many medical settings. The standard ECG record includes 12 lead waveforms, denoted as I, II, III, aVR, aVL, aVF, V1, V2, V3, V4, V5, and V6, arranged in a specific order that is interpreted by a physician using pattern recognition techniques. The ECG is acquired by physicians, nurses or other specially trained technicians using specialized hardware and equipment. In the usual configuration, 10 electrodes are placed on the body torso to measure the electrical potentials that define the standard 12 leads. Other lead systems have been tested over the years. These include the Frank vectorcardiogram ("VCG") system, which uses 3 nearly orthogonal leads denoted as X, Y, and Z; 4 right chest leads, denoted by V3R, V4R, V5R, and V6R; and 3 left posterior leads, denoted as V7, V8, and V9. No single manufacturer currently makes equipment that allows for the acquisition of all 22 leads. In order to acquire these leads, the technician must first remove the lead clips attached to the standard electrode placement sites and then re-attach them on the electrodes placed on the non-conventional sites. This requires at least 3 separate tracing acquisitions and a total of 21 electrode placements.

It is usual in the practice of medicine to place patients with potential cardiac abnormalities on a rhythm monitor, a specially designed hardware equipment that displays only one ECG lead but which has the capability of measuring 3 different leads. There are some manufacturers who have designed rhythm monitors that can display three leads as well but the usual display format is still one lead. With this equipment, the patient has 3 to 4 electrodes placed on the body torso to acquire the 3 different lead configurations. While the patient is connected to the rhythm monitor, if a standard 12 lead ECG is ordered, the technician will then place all of the additional electrodes for the separate acquisition of the ECG. Thus, the efficiency of acquiring an ECG would be improved if there existed a process by which the standard 12 lead ECG, the 3 lead VCG, the 4 right chest leads, or the 3 left posterior leads could be acquired instantaneously on demand from the rhythm monitor rather than the usual ECG machine, using fewer than standard number of electrodes.

Nicklas, et al., in U.S. Pat. No. 5,058,598, invented a system for synthesizing ECG leads based on developing a patient-specific transform. This system could synthesize a 12 lead ECG based on receiving data from 3 leads. However, this system required first acquiring a complete n-lead ECG from a patient in the usual manner in order to compute a patient specific transformation, which would then be applied subsequent ECG data acquired from that patient. This is cumbersome, as the resulting transformation is applicable to only one patient and needs to be stored in a medium that must be accessible for use during the patient's hospital stay.

In addition, the Nicklas transformation may also have a time dependency, indicating that the patient transform may change with time such that the transformation may need to be re-computed for each subsequent encounter with that patient for diagnostic accuracy.

Dower, in U.S. Pat. No. 4,850,370, used the Frank VCG 3 lead system to derive the 12 lead ECG, however, this system is not conventional and is unfamiliar to most clinical staff. Dower also developed another unconventional lead configuration known as the EASI system, but this configuration requires the acquisition of 4 leads to derive the 12 lead ECG.

SUMMARY OF THE INVENTION

The present invention solves the aforementioned problems by using the mathematical techniques of abstract factor analysis and the simplex optimization algorithm to derive a universal transformation matrix that is applicable to all patients and is independent of time. This universal transformation matrix is thus applicable when needed and does not require the acquisition of a complete n-lead ECG for each patient prior to its implementation.

In order to do this, one first measures and digitizes the voltage-time data for some set of ECG leads to define an ECG training set. Without limitation, examples of lead sets include the following formats:

12 leads: I, II, III, aVR, aVL, aVF, V1, V2, V3, V4, V5, V6;
15 leads: I, II, III, aVR, aVL, aVF, V1, V2, V3, V4, V5, V6, X, Y, Z;
15 leads: I, II, III, aVR, aVL, aVF, V1, V2, V3, V4, V5, V6, V7, V8, V9;
16 leads: I, II, III, aVR, aVL, aVF, V1, V2, V3, V4, V5, V6, V3R, V4R, V5R, V6R;
18 leads: I, II, III, aVR, aVL, aVF, V1, V2, V3, V4, V5, V6, V7, V8, V9, X, Y, Z;
19 leads: I, II, III, aVR, aVL, aVF, V1, V2, V3, V4, V5, V6, V7, V8, V9, V3R, V4R, V5R, V6R;
22 leads: I, II, III, aVR, aVL, aVF, V1, V2, V3, V4, V5, V6, V7, V8, V9, V3R, V4R, V5R, V6R, X, Y, Z.

Once the voltage-time data arrays have been acquired, the abstract factor analysis ("AFA") technique is applied to each ECG voltage-time data array training set in order to minimize the error in the measured arrays. The final step is then to apply the simplex optimization technique ("SOP") in order to derive a universal transformation matrix applicable to all patients, and is time independent. This universal transformation matrix can then be applied to a standard measured 3 lead subsystem to derive the standard 12 lead ECG as well as other systems, and can generate up to 22 leads to enable a more accurate interpretation of cardiac electrical activity. These derived ECG values are approximately 98% accurate when compared to observed lead measurements. The standard 3 lead system used to synthesize the 12 lead ECG are the measured I, aVF and V2 leads that belong to the standard 12-lead system. This measured lead set is conventional and familiar to clinical staff and are thus easy to apply. The application of abstract factor analysis and simplex optimization are described in the inventor's copending application, "SYSTEM AND METHOD FOR SYNTHESIZING LEADS OF AN ELECTROCARDIOGRAM", patent application Ser. No. 10/150,719, filed on May 17, 2002, the contents of which are incorporated herein by reference. Since this lead set approximates an orthogonal system, these lead vectors can be plotted against each other in a 3-dimensional space to yield a space curve whose properties can be correlated with coronary pathologies. The properties of the 3-dimensional spatial curve can be characterized by calculating the fractal indices of the curves, and the values of these fractal indices are predictive of acute cardiac syndromes.

The technique of fractal analysis abstract is well known in the applied mathematical art. The concept of a fractal index was first elucidated by Mandelbrot in *The Fractal Geometry of Nature*, Freeman, New York, 1983, incorporated herein by reference. For a discussion of the calculation of fractal indices of planar curves, see Katz, *Fractals and the Analysis of Waveforms*, Comput. Biol. Med. 18:3, pp. 145–156 (1988), the contents of which are incorporated herein by reference.

BRIEF DESCRIPTION OF THE DRAWINGS

FIG. 17 depicts a table of lead values and fractal indices.

DETAILED DESCRIPTION OF THE INVENTION

Figure 4:
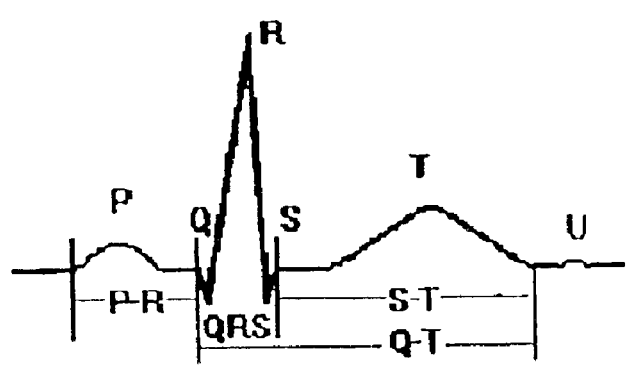
FIG. 4 depicts a typical cardiac electrical cycle as measured by an ECG.

The full cycle of cardiac activity is represented by a wave known as the PQRST wave, defined by Einthoven, *Arch. ges Phys.* 150:275, 1913, reprinted in *Am. Heart J.* 40:163, 1950, translation by H. E. Huff and P. Sekelj. This wave represents full contraction and relaxation of the heart. An example of a PQRST wave is shown in FIG. 4. One complete heart cycle averages 1/72 seconds.

Abstract Factor Analysis

Figure 1:
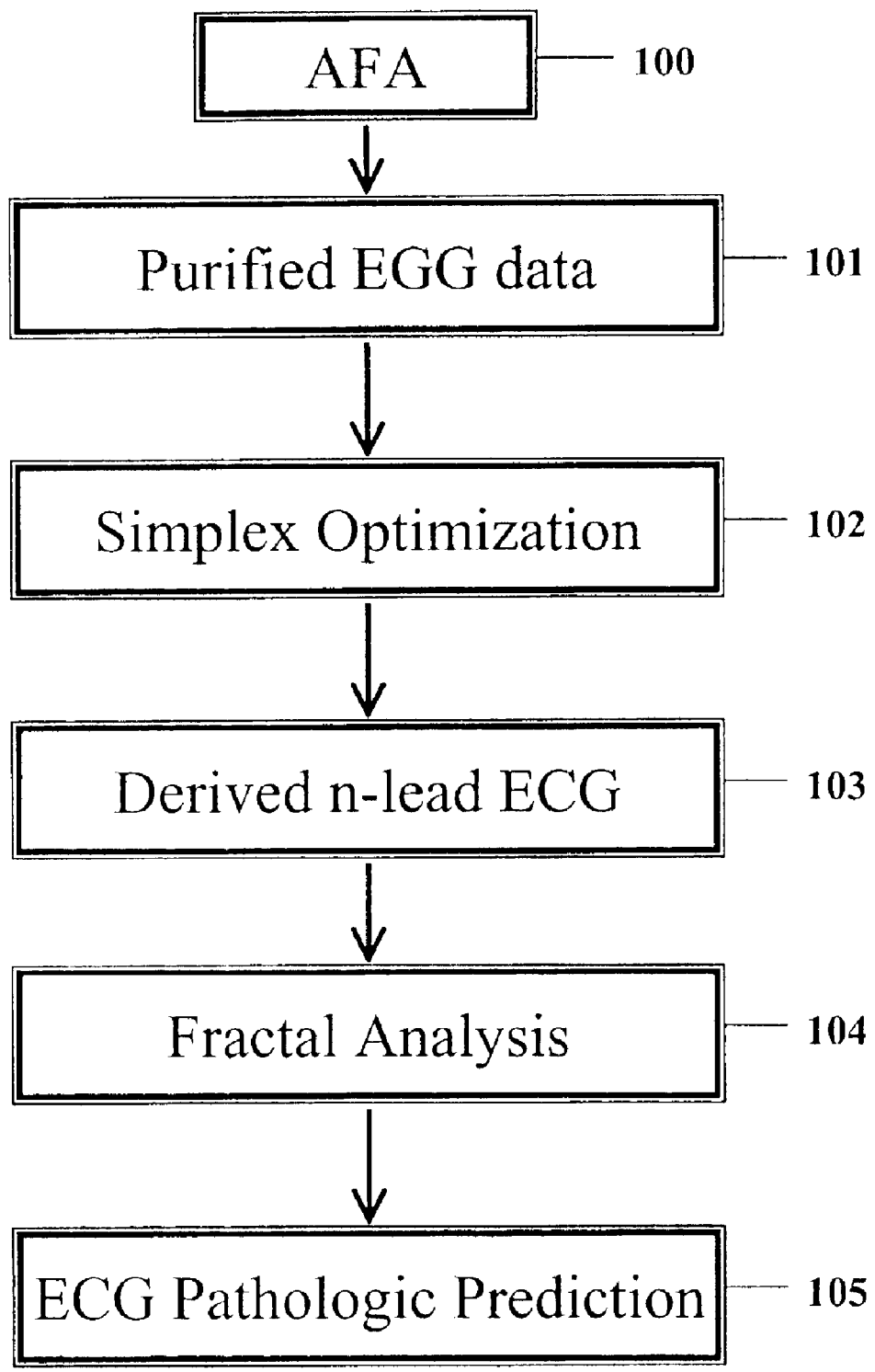
FIG. 1 depicts a flow diagram of how the universal transformation matrix of the present invention is calculated and used.
Figure 2:
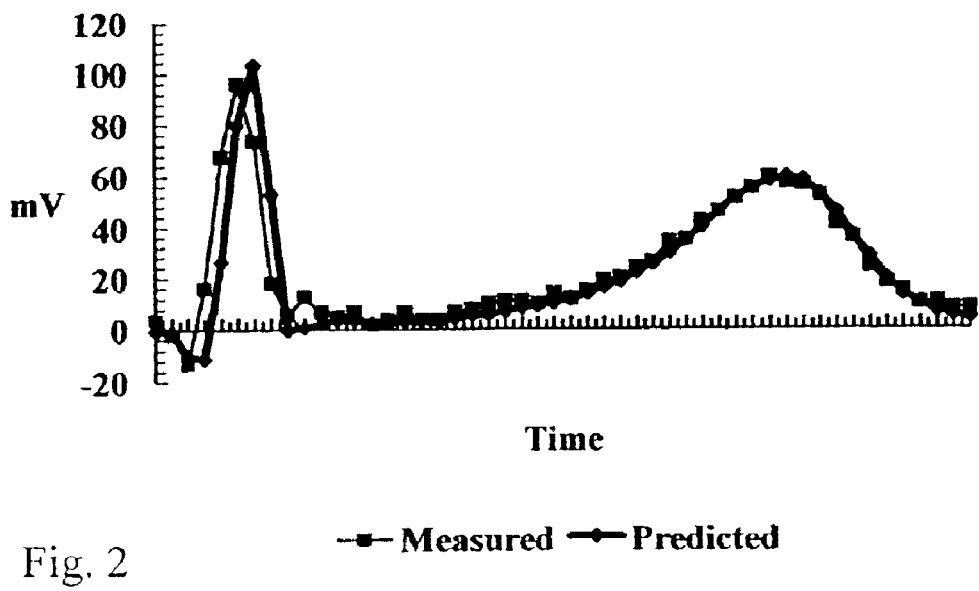
FIG. 2 depicts a comparison of a measured ECG against one predicted by the application of the universal transformation matrix of the invention.

A flow chart illustrating the overall process of the invention is depicted in FIG. 1. The first step, shown in block 100, is the application of abstract factor analysis to a training data set. Abstract factor analysis ("AFA") is applied to the entire n-lead ECG measured data matrix in this invention to "pretreat" the training set of ECGs, from which the transformation matrix is derived via simplex optimization, so as to minimize the inherent error in this training set. The advantage of AFA is that this technique removes predictable error, such as a wandering baseline, baseline noise, and lead placement errors, from a data set, yielding an improved, measured, data set. A comparison of ECG values for lead I as measured and as predicted through AFA is shown in FIG. 2, showing close agreement.

For the purpose of AFA, the ECG can be represented in an n-dimensional system by a linear sum of product terms. The standard 12-lead ECG is a system where n=12. At a particular time t, the 12-lead ECG can be represented as $$V(t)=V_1(t)L_1+V_2(t)L_2+\ldots+V_n(t)L_n,$$

where V is a 12-dimensional vector, $V_m$ is the potential at the $m^{th}$ lead, $L_m$ is a unit vector in the 12-dimensional space, and t is time. The potential V(t) can also be represented by a set of orthogonal basis vectors {X} that spans the space:

$$V(t)=\sum_{m=1}^{n}K_m(t)X_m.$$

Abstract factor analysis identifies n, the number of factors influencing the data set, K, the transformation coefficient matrix, and X, the abstract lead-vector set.

To perform AFA, we consider an N×M data matrix [V] of voltage-time measurements, where N is the number of leads, and M is the number of data points. In AFA, a covariance matrix is diagonalized to yield a set of eigenvalues $\lambda_j$ that can be ordered by magnitude. The covariance matrix can be defined as $[Z]=[V]^T[V]$, which is an M×M matrix with up to M eigenvalues, or it can be defined as $[Z]=[V][V]^T$, N×N matrix with up to N eigenvalues. Each eigenvalue $\lambda_j$ corresponds to an orthogonal basis eigenvector $X_j$. The diagonalization procedure involves finding a matrix $[Q_j]$ that diagonalizes [Z]: $[Z][Q_j]=\lambda_j[Q_j]$. In the context of ECGs, M is typically 300 measurements over one complete cycle. Multiple training sets of the N×M matrix are subjected to the AFA technique.

Figure 3:
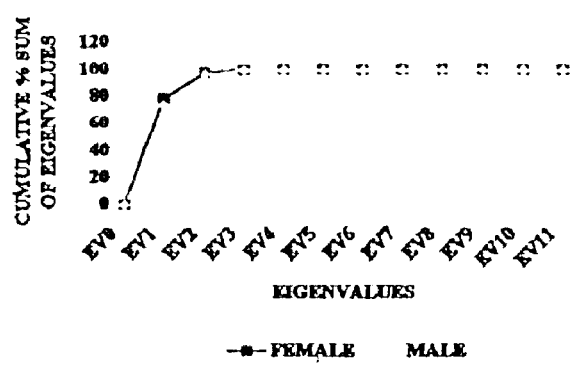
FIG. 3 depicts the cumulative percentage variance as a function of the number of eigenvalues as determined by abstract factor analysis.

From the application of AFA to the data set we find that 3 leads can account for almost all of the information content in an n-lead ECG, where n=12 to 22 leads. This can be demonstrated by means of the cumulative percentage variance. The variance can be defined as:

$$\text{Var}=\lambda_j\Big/\sum_{k=1}^{n}\lambda_k,$$

where n=12 . . . 22 and $\lambda_j$ is the magnitude of the $j^{th}$ eigenvalue. The cumulative percentage variance is defined as $$\text{Cum \% Var}=\sum_{k=1}^{c}\lambda_k\Big/\sum_{k=1}^{n}\lambda_k,$$

where c=$c^{th}$ eigenvalue in the sequence of eigenvalues $\lambda_j$ ordered by magnitude. The cumulative percentage variance is thus a measure of the information content of the system. FIG. 3 is a graph of the cumulative percentage variance as a function of $\lambda_j$ and illustrates that most of the information content of the system is contained in the first 3 eigenvalues.

In fact, AFA demonstrates that 3 leads can account for approximately 98–99% of the information content of a 12-lead ECG. Thus, for a 12-lead system, the resulting transformation matrix [K] is a 3×12 matrix of purified ECG data, as indicated in block 101 of FIG. 1. Given a set of M voltage-time measurements for 3 leads, the full 12 lead set of measurements can be calculated by multiplying the transformation matrix [K] by the 3×M voltage-time data matrix for the 3 measured leads. This result can easily be generalized to a system with an arbitrary number of leads, hence our n-lead ECG terminology.

Simplex Optimization

The next step in the derivation of the universal transformation matrix of the present invention was application of the simplex optimization technique ("SOP") to the training set that was subjected to AFA, indicated in block 102 of FIG. 1. Since 3 leads account for almost all of the information of an n-lead ECG, SOP was applied to a 3-lead set comprised of {I, aVF, V2} to calculate to other leads.

Simplex optimization, which is different from the simplex algorithm used for minimizing constrained linear systems, is a method for finding a maximum for a multiple variable function when the underlying function may be unknown. A simplex is a geometric figure defined by a number of points (n+1) that is one more than the number of variables. For a function of two variables z=f(x, y), one starts with 3 points $\{(x_1, y_1), (x_2, y_2), (x_3, y_3)\}$, and the value of the function is measured for those 3 points. These 3 points are then labeled as "B", "N", and "W", for, respectively, the best, next best (or next worst), and worst values. Since we are seeking a maximum point, the best value has the greatest magnitude.

The next point R for measuring the function f is determined by R=P+(P−W), where P is the centroid of the figure when the worst value point is eliminated.

Once the function has been measured for R, there are 3 possibilities for the next step. First, if the value for R is better than the value for B, an expansion is attempted with a new point defined by E=P+2(P−W). If the value for E is better than B, E is retained and the new simplex is defined by N, B, and E. If the value for E is not better than that for B, the expansion is said to have filed and the new simplex is defined by B, R, and N.

Second, if the value for R is between that for B and N, the new simplex is defined to be B, R, and N, and the process is restarted.

Finally, if the value for R is less desirable than that for N, a step was made in the wrong direction, and a new simplex should be generated. There are 2 possibilities. If the value for R is between that for N and W, the new point should be closer to R than W: $C_R$=P+0.5 (P−W), and the new simplex is defined by B, N, and $C_R$. If the value at R is worst than the value at W, then the new point should be closer to W than R: $C_W$=P−0.5(P−W). The new simplex is then defined by B, N, and $C_W$. The process is iterated until a maximum is found.

Figure 5:
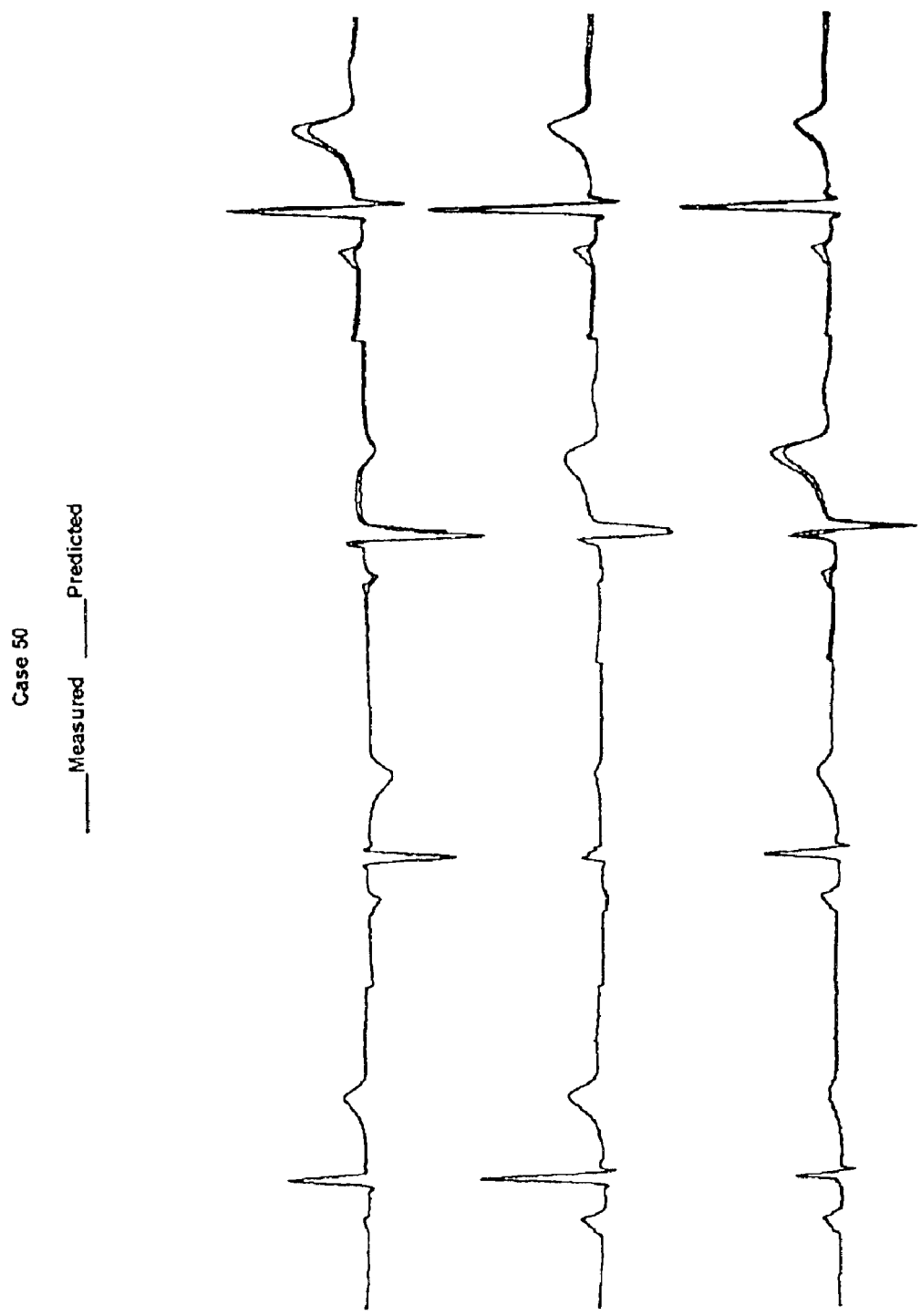
FIG. 5 depicts an ECG printout that compares measured values against values derived through the simplex optimization method.

For the case of the 3-lead ECG, the values of the other leads are calculated as functions of a 3-lead set, preferably {I, aVF, V2}. Thus, the simplex will be a 3-dimensional figure defined by 4 points that represent the starting values of {I, aVF, V2}. The results of this optimization were used to define, at step 103, an N×3 universal transformation matrix [K] such that when multiplied by a vector comprising the 3 leads {I, aVF, V2} for a particular time yield a full n-lead ECG. In particular, the [K] matrix was calculated for the full PP cycle of the heart beat as well for segments within the PP cycle, such as the PR interval, the QRS interval, the SP interval, and the QT interval. The accuracy of the optimization was checked and validated by comparing the derived values and coefficients for the II, III, aVR, and aVL leads with measured values for those leads. A comparison of a synthesized ECG based on values derived from simplex optimization with a measured ECG is depicted in FIG. 5.

Spatial Loops

As stated above, the inventor has verified through the application of AFA that ~98–99% of the information displayed thereon can be reproduced from the measurement of just 3 leads. Since these leads are approximately orthogonal, values takes at the same time can be plotted against each other in 3-dimensional space, resulting in a spatial ECG loop. Virtually all of the information in a 12-lead ECG is in the 3-dimensional spatial ECG loop. In addition, the inventor has verified that the information content of lead configurations of up to 22 leads can be reproduced from just 3 measured leads. By increasing the lead space to 22 leads, clinicians can more accurately diagnose cardiac pathology, such as right heart infarction or posterior infarction.

Figure 6:
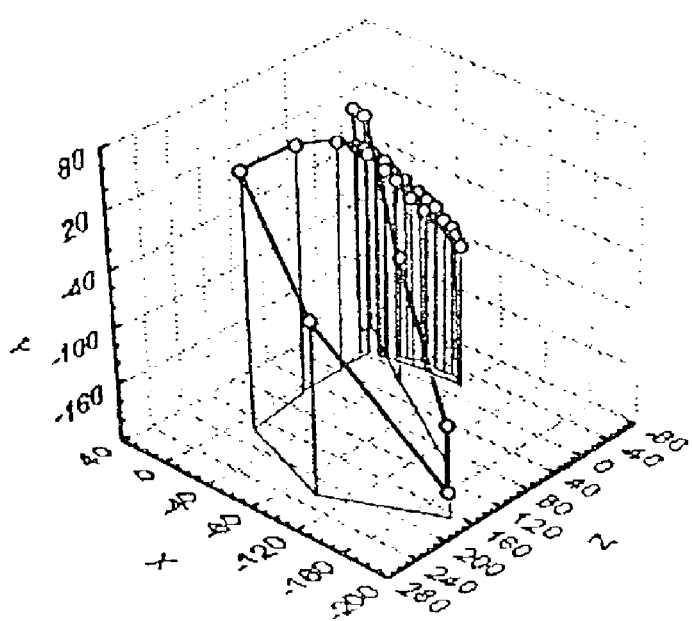
FIG. 6 depicts a normal 3-dimensional spatial ECG loop.
Figure 7:
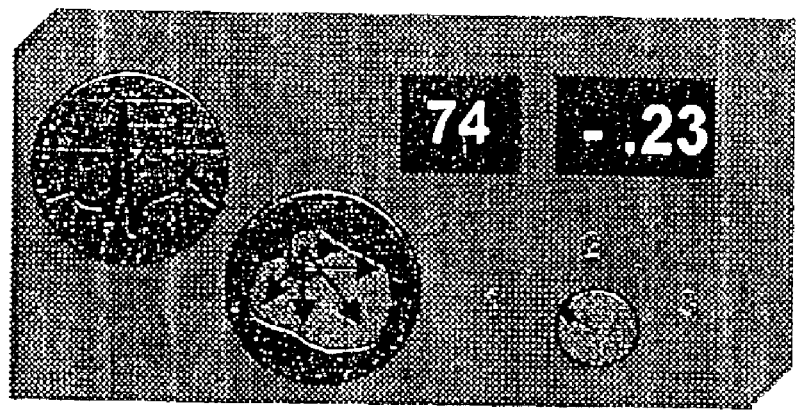
FIG. 7 depicts a portable bedside heart monitor.
Figure 8:
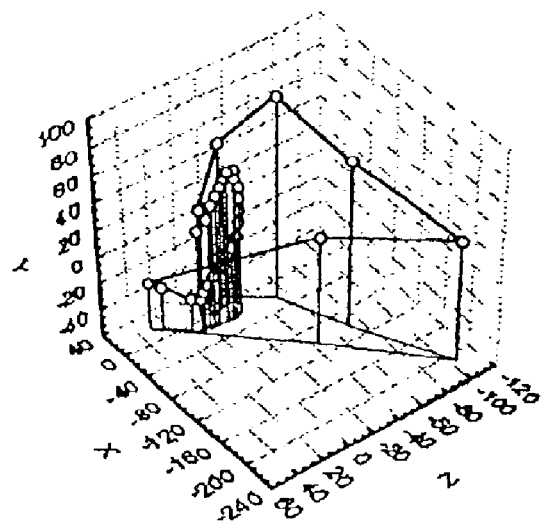
FIG. 8 depicts a 3-dimensional spatial ECG loop that represents an acute inferior MI.
Figure 9:
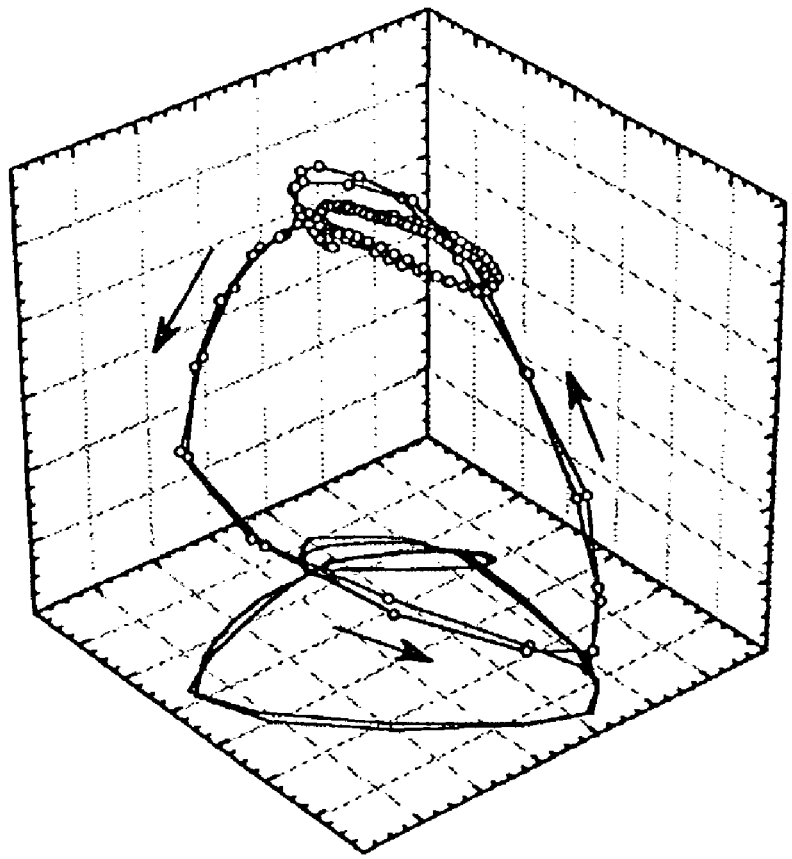
FIG. 9 depicts the vectorial forces of cardiac potentials in a 3-dimensional spatial ECG loop.
Figure 12:
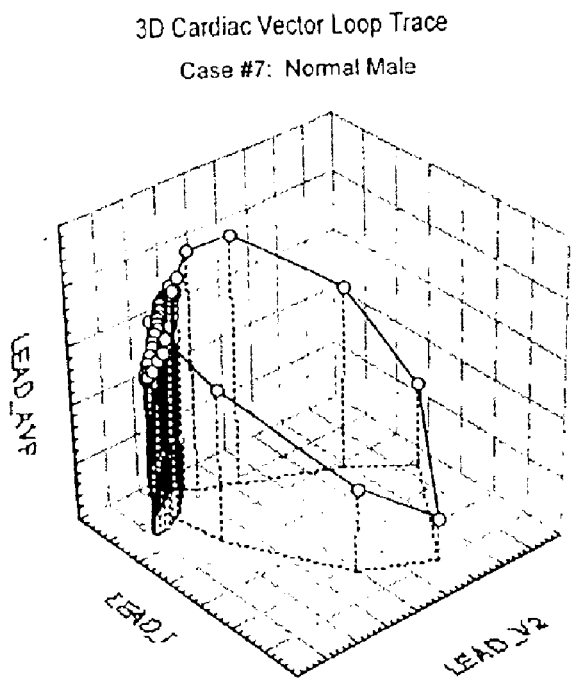
FIG. 12 depicts the 3-dimensional spatial ECG loop for a normal male heart.
Figure 13:
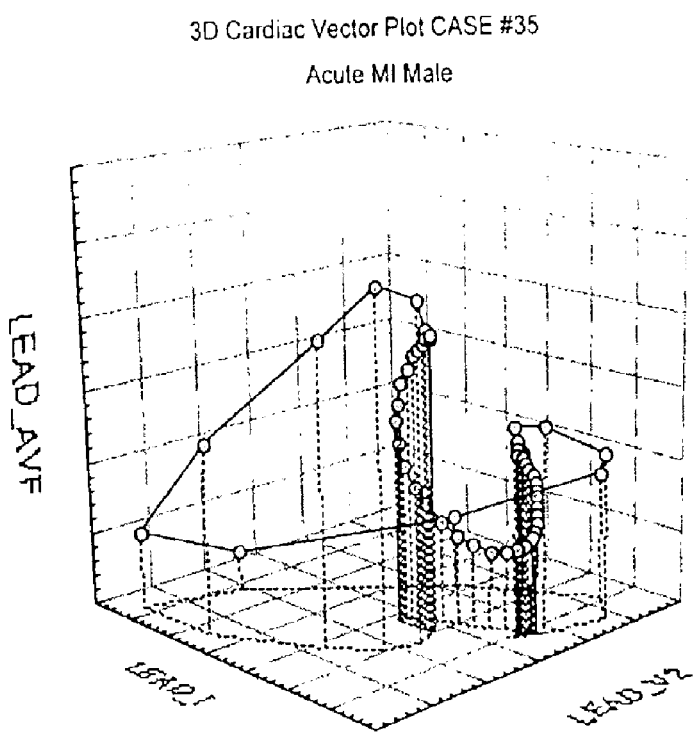
FIG. 13 depicts the 3-dimensional spatial ECG loop for a male heart exhibiting acute MI.

A typical 3-dimensional ("3D") spatial loop for a normal male heart is shown in FIG. 6. This type of display can easily be built into a standard heart monitor, shown in FIG. 7, that incorporates the single wave configuration as currently exists. This spatial loop can also be printed for the patient medical record. The 3D spatial loop displayed in FIG. 8 represents an acute inferior MI. When compared with the display of normal heart function depicted in FIG. 6, it can be seen that the vector forces traveling in the timed sequence are clearly different. Another example of the comparison of 3D spatial loops for normal cardiac activity versus acute MI cardiac activity can be found in FIGS. 12 and 13. The vectorial forces of cardiac potentials are shown in a counterclockwise 3D spatial ECG loop depicted in FIG. 9. In additional to providing diagnostic information, the 3-dimensional spatial ECG loops can serve as teaching devices to educate clinicians in the field of cardiac electrophysiology.

Figure 10:
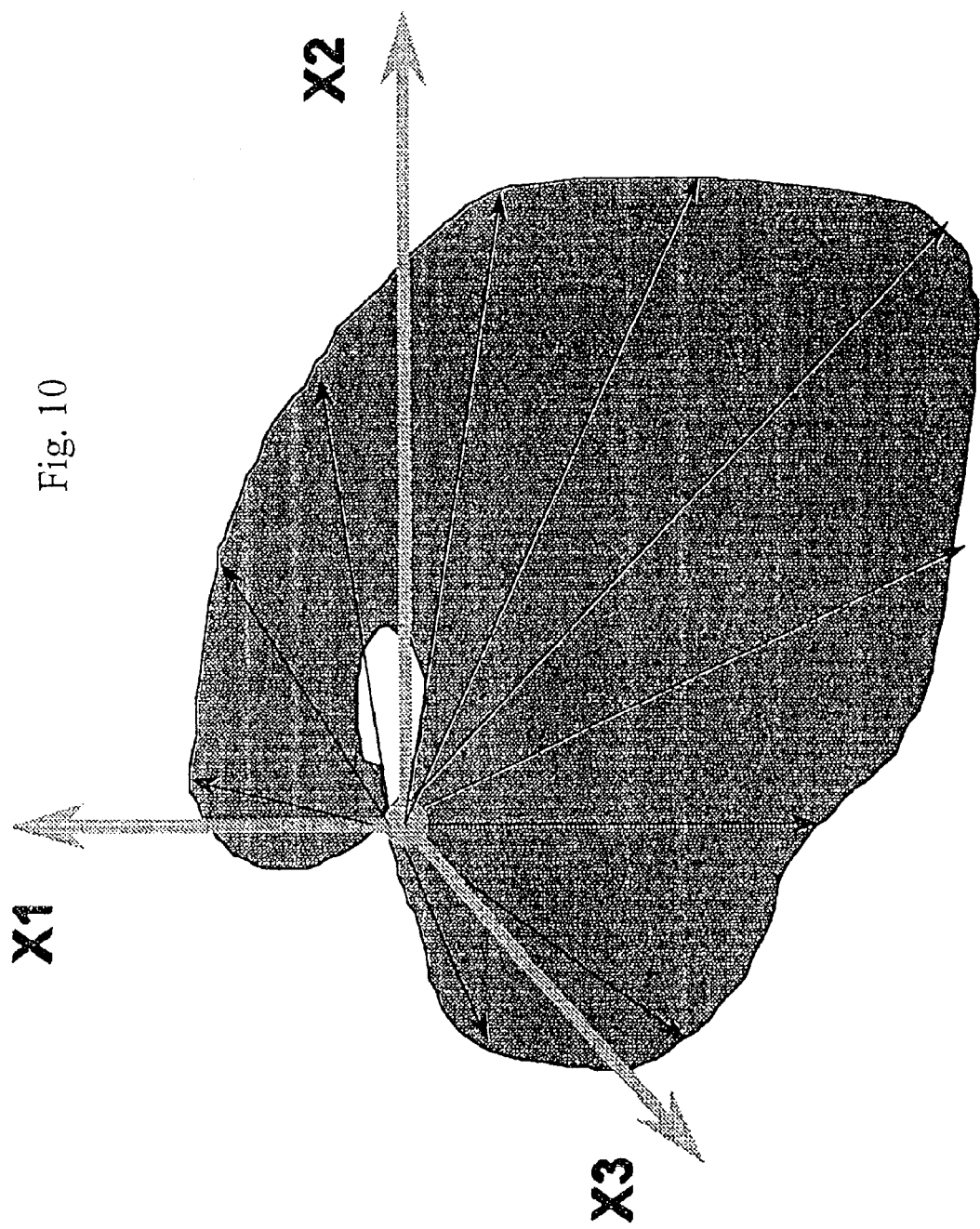
FIG. 10 depicts how a 3-dimensional spatial ECG loop is traced out over time.

In general, the cardiac electrical vector traces a loop in time in N-dimensions, where N is the number of leads. Abstracts factor analysis has demonstrated that we can take N as equal to 3, and thus we plot leads I, aVF and V2 against each other as they are approximately orthogonal. However, there is no fundamental reason why the spatial loop cannot be regarded as a curve in an N-dimensional space, where N is the number of leads. This spatial loop has a defined surface area, defined by triangles swept out by the loop vector as it advances in time. This is illustrated in FIG. 10. The length structure and surface area defined by this spatial loop can yield information characterizing the pathologic state of a patient. In particular, a fractal index can be calculated from the spatial loop at step 104 of FIG. 1, and the value of this index can predict the presence or absence of pathologic acute coronary syndromes ("ACS") at step 105 of FIG. 1. This index can also serve as a trigger upon which the synthesized ECG can be automatically printed, saving time and money, and possibly a patient's life as the diagnosis of ACS can be made at the point of service, possible before symptoms develop.

Figure 11:
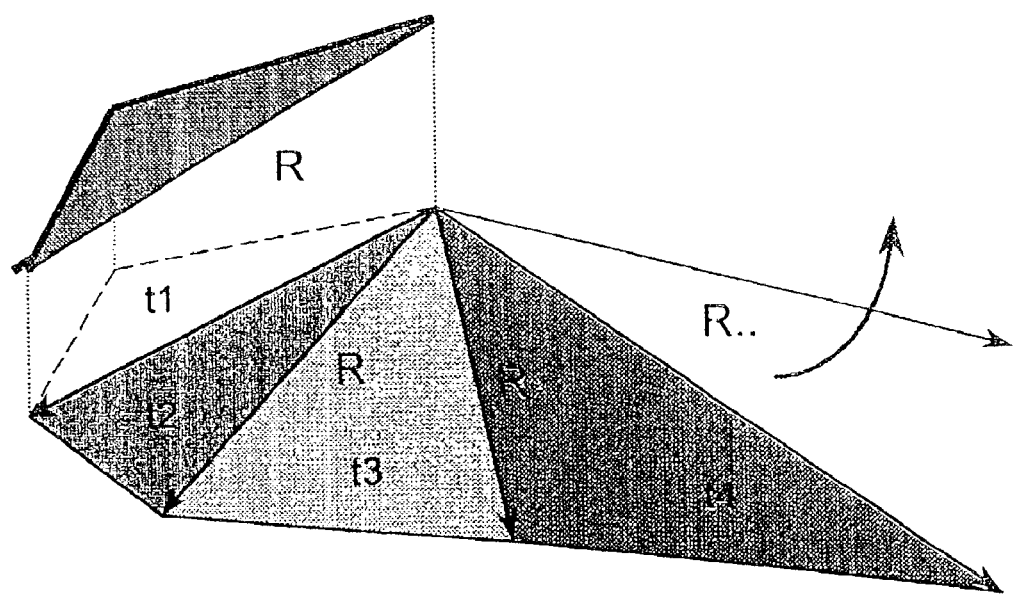
FIG. 11 depicts the area triangles of the 3-dimensional spatial ECG loop.

This spatial curve can be characterized by various fractal indices. The time rate of change in index values from a baseline value are also predictive of cardiac activity. As the potential ECG vector loop traces a loop in space over time with each heart beat, a fractal index can be calculated from the sequence of triangles formed with area A(t) and perimeter L(t), as shown in FIG. 11. The variance in a function of the fractal index on a beat-to-beat basis is a measurement of autonomic activity. These fractal indices can be calculated by a device such as the modified portable bedside heart monitor depicted in FIG. 7.

One method of calculating a fractal index for a spatial loop useful in the analysis of ECGs is based on a calculation of a fractal index adapted for a planar curve as described in Katz for 2 dimensional X-Y data. A fractal dimension D of a planar curve is defined as D=log(L)/log(d), where L is the total length of the curve, and d is the diameter or planar extent of the curve. The length can be defined in terms of an average step size or distance between successive points, a, and a number of steps in a curve n, as n=L/a, in which case the fractal dimension D=log(n)/(log(n)+log(d/L)). The Katz paper provides examples of this formula applied to several basic waveforms of 30 points each in Katz's FIG. 1.

The method of Katz's formula for D in X-Y data can be readily applied to the spatial loops defined by the ECG lead values, for spatial loops in any dimension. In order to define the fractal dimension for an N-dimensional loop, it is useful to define some preliminary quantities. First, we define $$D(t_k) = \left(\sum_{i=1}^{N} x_i^2(t_k)\right)^{\frac{1}{2}}$$

$$L(t_k) = \left(\sum_{i=1}^{N} (x_i(t_k) - x_i(t_{k-1}))^2\right)^{\frac{1}{2}}$$

$$DD(t_k) = \max(D(t_k), DD(t_{k-1}))$$

and $$LSUM(t_k) = LSUM(t_{k-1}) + L(t_k),$$

where $x_i(t_k)$ represents the value of the $i^{th}$ ECG lead in an N-lead ECG at time $t_k$. It can be seen that D is a length in an N-dimensional space, while L is an arc segment in the N-dimensional space defined by the difference between $D(t_k)$ and $D(t_{k-1})$, the length at the previous time $t_{k-1}$. The time $t_k$ can be thought of as kδt, where δt is a unit of time. Then, we define a fractal dimension as a function of time k as $$FD(k) = \log(k)/(\log(k) + \log(DD(t_k)/LSUM(t_k))).$$

FIG. 17 depicts a spreadsheet table of lead values measured 46 times over the ST-segment of the cardiac cycle. These lead values are for the standard 12-lead set, which is I, II, III, aVR, aVL, aVF, V1, V2, V3, V4, V5, and V6. The columns labeled "D", "L", "DD", "LSUM", and the "Y" column of "FD" correspond to values for, respectively, $D(t_k)$, $L(t_k)$, $DD(t_k)$, $LSUM(t_k)$, and FD(k), as defined above. The columns labeled "ST" and "X" are values of the time interval counter, k.

Figure 14:
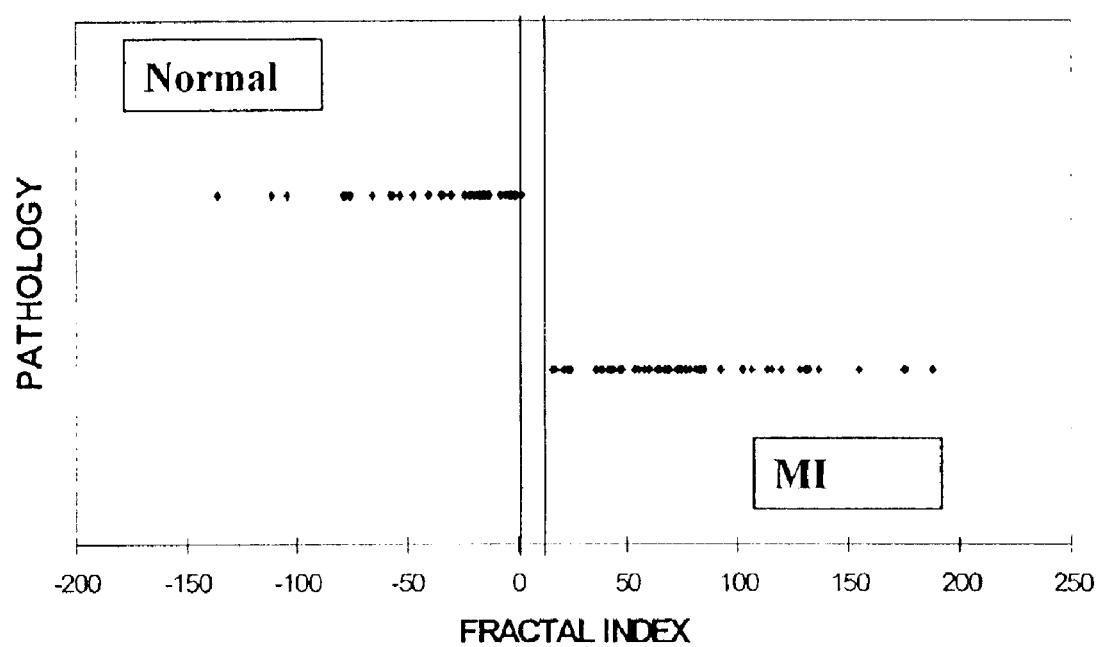
FIG. 14 illustrates the separation of fractal indices for normal versus MI heart activity.
Figure 15:
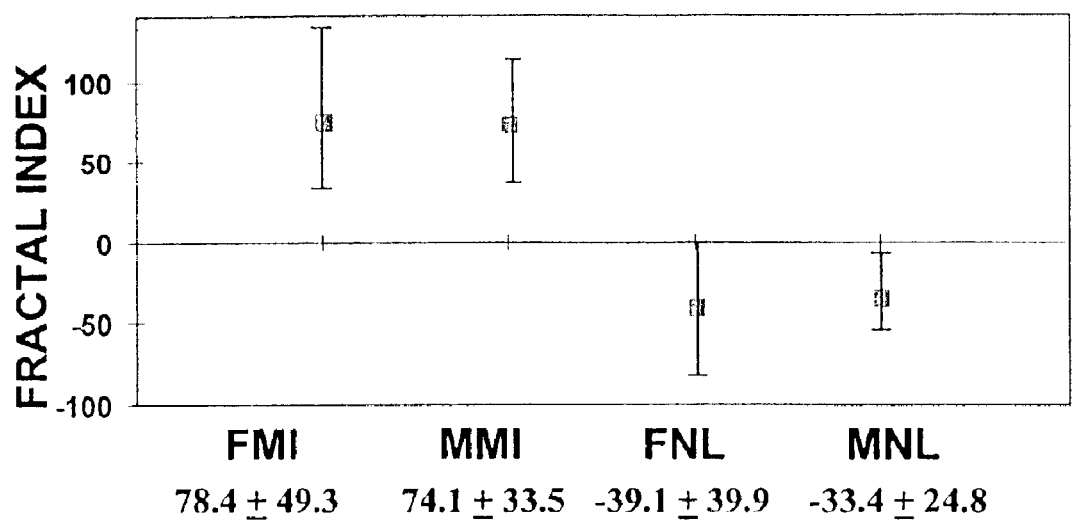
FIGS. 15 and 16 illustrate the separation of values of fractal indices for both female and male hearts for both normal and MI cardiac activity.
Figure 16:
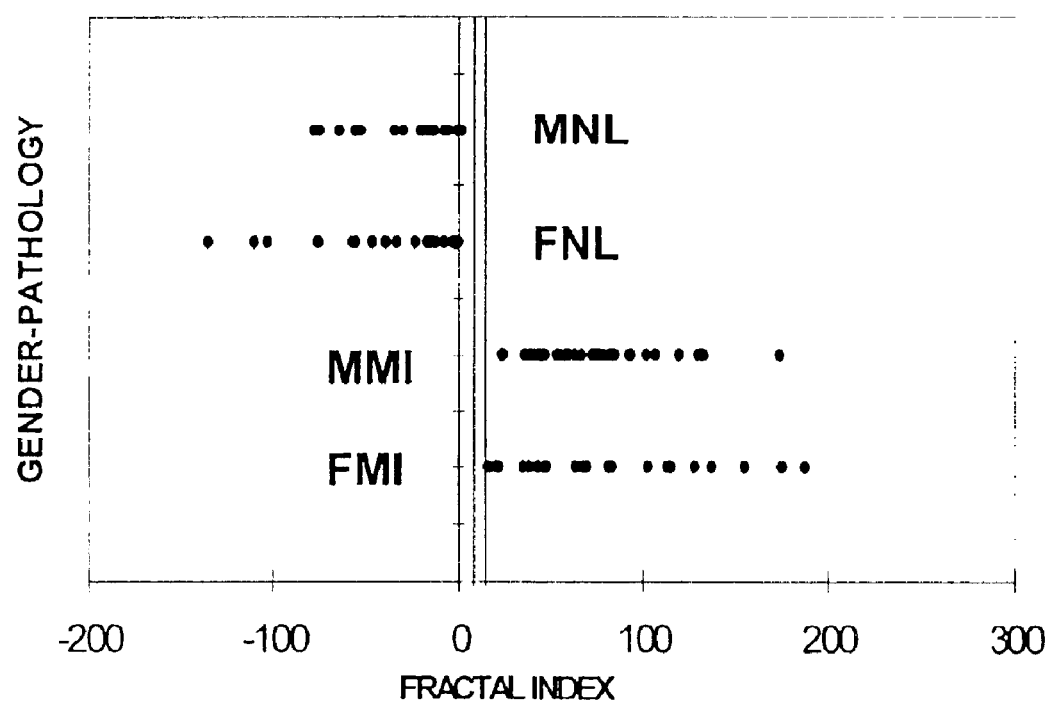

The time rate of change of FD as a function of k as k increases, referred to as the time derivative of FD, can also be readily calculated for the spatial loops. The inventor has found that the time derivative of FD, hereinafter referred to as FD', is an excellent predictor of ACS because FD' separates into negative and positive values based on normal versus abnormal cardiac activity, respectively. This separation of values is graphically illustrated in FIGS. 14, 15 and 16. Thus, the crossover of FD' from negative to positive values can serve as a trigger for generating an alarm and for automatically printing the synthesized ECGs, saving time and money, and possibly a patient's life. The fact that the crossover of FD' is predictive of the onset of MI allows the diagnosis of ACS to be made at the point of service, possibly before symptoms of ACS actually develop. This time difference can make the difference in saving a patient's life.

There are other fractal indices useful for predicting abnormal cardiac function. In order to define these, we need some additional preliminary quantities:

$$PerimTot(t_k) = D(t_k) + LSUM(t_k)$$

$$Area(t_k) = \frac{1}{4}((D(t_k) + D(t_{k-1}) + L(t_k))(D(t_k) - D(t_{k-1}) + L(t_k))(-D(t_k) + D(t_{k-1}) + L(t_k))(D(t_k) + D(t_{k-1}) - L(t_k)))^{\frac{1}{2}}$$

and $$SumArea(t_k) = SumArea(t_{k-1}) + Area(t_k).$$

We can now define two additional fractal indices:

$$K1 = (LSUM(t_k)^\cdot FD(k))/SumArea(t_k)$$

and $$K2 = (PerimTot(t_k)^\cdot FD(k))/SumArea(t_k).$$

Once again, the time derivatives of these indices as a function of k is an excellent predictor of ACS because the time derivative again separates into negative and positive values based on normal versus abnormal cardiac activity, respectively.

The fractal indices presented are only a sampling of possible fractal indices possible for the analysis of ECG spatial loops. For a general discussion of other measures of fractal dimension, see Francis C. Moon, *Chaotic and Fractal Dynamics*, John Wiley & Sons, Inc., Chapter 7, the contents of which are incorporated herein by reference.

The method of the invention can be implemented on any computer system using any available programming language. One embodiment of the invention is implemented using Microsoft Visual Basic executing on a personal computer running the Windows operating system. The invention is not limited to this implementation, however, and implementations is other programming languages executing on other machines, such as the Mackintosh, or workstations running under the Unix operating system or variants thereof, such as Linux, are within the scope of the invention.

Alternatively, the method of the invention can be implemented in a standard heart monitor that has been modified to acquire 3 leads in phase, display a 3D spatial loop, calculate a fractal index for that loop and monitor the time rate of change of the fractal index. These modifications can be accomplished by the addition of dedicated computer hardware and software to the monitor. This software can be programmed with the universal transformation matrix claimed in the inventor's co-pending application to calculate an N-lead ECG from the three acquired leads, and to display the spatial loop and to calculate the fractal index and monitor its time rate of change. In addition, the modified monitor can print the full N-lead ECG and sound or indicate an alarm when a change in the time derivative of the fractal index indicates the onset of cardiac pathology.

While the present invention has been described and illustrated in various preferred and alternate embodiments, such descriptions and illustrations are not to be construed to be limitations thereof. Accordingly, the present invention encompasses any variations, modifications and/or alternate embodiments with the scope of the present invention being limited only by the claims which follow.

What is claimed is:

1. A method for predicting cardiac pathology comprising the steps of:

acquiring a plurality of lead values as a function of time for a set of electrocardiogram leads;

defining a spatial curve from the lead values for at least three leads;

calculating a fractal index as a function of time for the spatial curve; and monitoring the time rate of change of the fractal index.

2. The method of claim 1, further comprising the step of calculating the lead values from electrode readings taken from electrodes attached to a patient.

3. The method of claim 1, wherein a negative time rate of change of the fractal index is indicative of normal cardiac activity, and a positive time rate of change of the fractal index is indicative of pathological cardiac activity.

4. The method of claim 1, wherein the set of electrocardiogram leads comprises from 3 to about 80 leads, and wherein the full set of electrocardiogram leads can be calculated from a subset of at least 3 electrocardiogram leads by using a universal transformation matrix.

5. The method of claim 1, wherein the fractal index is defined by the equation $$FD(k)=\log(k)/(\log(k)+\log(DD(t_k)/LSUM(t_k))),$$

wherein:

$t_k=k\delta t$ is the time after k intervals of time unit $\delta t$;

$$LSUM(t_k) = LSUM(t_{k-1}) + \left(\sum_{i=1}^{N}(x_i(t_k) - x_i(t_{k-1}))^2\right)^{\frac{1}{2}};$$

$$DD(t_k) = \max\left(\left(\sum_{i=1}^{N} x_i^2(t_k)\right)^{\frac{1}{2}}, DD(t_{k-1})\right);$$

N represents the number of electrocardiogram leads; and $x_i(t_k)$ represents the value of the $i^{th}$ lead in the N-lead set at time $t_k$.

6. The method of claim 1, wherein the fractal index is defined by the equation $$K1=(LSUM(t_k) \cdot FD(k))/SumArea(t_k)$$

wherein $t_k=k\delta t$ is the time after k intervals of time unit $\delta t$;

$$LSUM(t_k) = LSUM(t_{k-1}) + \left(\sum_{i=1}^{N}(x_i(t_k) - x_i(t_{k-1}))^2\right)^{\frac{1}{2}};$$

$$FD(k)=\log(k)/(\log(k)+\log(DD(t_k)/LSUM(t_k)));$$

$$DD(t_k) = \max\left(\left(\sum_{i=1}^{N} x_i^2(t_k)\right)^{\frac{1}{2}}, DD(t_{k-1})\right);$$

$$SumArea(t_k) = SumArea(t_{k-1}) +$$
$$\frac{1}{4}((D(t_k) + D(t_{k-1}) + L(t_k))(D(t_k) - D(t_{k-1}) +$$
$$L(t_k))(-D(t_k) + D(t_{k-1}) + L(t_k))(D(t_k) +$$
$$D(t_{k-1}) - L(t_k)))^{\frac{1}{2}},$$

where $D(t_k) = \left(\sum_{i=1}^{N} x_i^2(t_k)\right)^{\frac{1}{2}}$ and $$L(t_k) = \left(\sum_{i=1}^{N}(x_i(t_k) - x_i(t_{k-1}))^2\right)^{\frac{1}{2}};$$

N represents the number of electrocardiogram leads; and $x_i(t_k)$ represents the value of the $i^{th}$ lead in the N-lead set at time $t_k$.

7. The method of claim 1, wherein the fractal index is defined by the equation $$K1=(PerimTot(t_k) \cdot FD(k))/SumArea(t_k)$$

wherein $t_k=k\delta t$ is the time after k intervals of time unit $\delta t$;

$$PerimTot(t_k) = \left(\sum_{i=1}^{N} x_i^2(t_k)\right)^{\frac{1}{2}} + LSUM(t_k)$$

$$LSUM(t_k) = LSUM(t_{k-1}) + \left(\sum_{i=1}^{N}(x_i(t_k) - x_i(t_{k-1}))^2\right)^{\frac{1}{2}};$$

$$FD(k)=\log(k)/(\log(k)+\log(DD(t_k)/LSUM(t_k)));$$

$$DD(t_k) = \max\left(\left(\sum_{i=1}^{N} x_i^2(t_k)\right)^{\frac{1}{2}}, DD(t_{k-1})\right);$$

$$SumArea(t_k) = SumArea(t_{k-1}) +$$
$$\frac{1}{4}((D(t_k) + D(t_{k-1}) + L(t_k))(D(t_k) - D(t_{k-1}) +$$
$$L(t_k))(-D(t_k) + D(t_{k-1}) + L(t_k))(D(t_k) +$$
$$D(t_{k-1}) - L(t_k)))^{\frac{1}{2}};$$

where $D(t_k) = \left(\sum_{i=1}^{N} x_i^2(t_k)\right)^{\frac{1}{2}}$ and $$L(t_k) = \left(\sum_{i=1}^{N}(x_i(t_k) - x_i(t_{k-1}))^2\right)^{\frac{1}{2}};$$

N represents the number of electrocardiogram leads; and $x_i(t_k)$ represents the value of the $i^{th}$ lead in the N-lead set at time $t_k$.

8. The method of claim 1, further comprising the step of displaying the spatial loop in a heart monitor.

9. The method of claim 1, further comprising the steps of displaying the fractal index values in a heart monitor and storing said fractal index values in said heart monitor.

10. An apparatus for monitoring cardiac activity comprising:
- means for acquiring a plurality of lead values as a function of time for a set of electrocardiogram leads;
- means for defining a spatial curve from the lead values of at least three leads;
- means for calculating a fractal index as a function of time for the spatial curve; and
- means for monitoring the time rate of change of the fractal index.

11. The apparatus of claim 10, further comprising means for calculating the lead values from electrode readings taken from electrodes attached to a patient.

12. The apparatus of claim 10, wherein a negative time rate of change of the fractal index is indicative of normal cardiac activity, and a positive time rate of change of the fractal index is indicative of pathological cardiac activity.

13. The apparatus of claim 10, wherein the set of electrocardiogram leads comprises from 3 to about 80 leads, and further comprising means for calculating the full set of electrocardiogram leads from a subset of at least 3 electrocardiogram leads by using a universal transformation matrix.

14. The apparatus of claim 10, wherein the fractal index is defined by the equation $$FD(k)=\log(k)/(\log(k)+\log(DD(t_k)/LSUM(t_k))),$$

wherein:

$t_k = k\delta t$ is the time after k intervals of time unit $\delta t$;

$$LSUM(t_k) = LSUM(t_{k-1}) + \left(\sum_{i=1}^{N}(x_i(t_k) - x_i(t_{k-1}))^2\right)^{\frac{1}{2}};$$

$$DD(t_k) = \max\left(\left(\sum_{i=1}^{N}x_i^2(t_k)\right)^{\frac{1}{2}}, DD(t_{k-1})\right);$$

N represents the number of electrocardiogram leads; and $x_i(t_k)$ represents the value of the $i^{th}$ lead in the N-lead set at time $t_k$.

15. The apparatus of claim 10, wherein the fractal index is defined by the equation $$K1=(LSUM(t_k)\cdot FD(k))/SumArea(t_k)$$

wherein $t_k = k\delta t$ is the time after k intervals of time unit $\delta t$;

$$LSUM(t_k) = LSUM(t_{k-1}) + \left(\sum_{i=1}^{N}(x_i(t_k) - x_i(t_{k-1}))^2\right)^{\frac{1}{2}};$$

$$FD(k)=\log(k)/(\log(k)+\log(DD(t_k)/LSUM(t_k)));$$

$$DD(t_k) = \max\left(\left(\sum_{i=1}^{N}x_i^2(t_k)\right)^{\frac{1}{2}}, DD(t_{k-1})\right);$$

$$SumArea(t_k) = SumArea(t_{k-1}) + \frac{1}{4}((D(t_k) + D(t_{k-1}) + L(t_k))(D(t_k) - D(t_{k-1}) + L(t_k))(-D(t_k) + D(t_{k-1}) + L(t_k))(D(t_k) + D(t_{k-1}) - L(t_k)))^{\frac{1}{2}},$$

where $D(t_k) = \left(\sum_{i=1}^{N}x_i^2(t_k)\right)^{\frac{1}{2}}$ and $$L(t_k) = \left(\sum_{i=1}^{N}(x_i(t_k) - x_i(t_{k-1}))^2\right)^{\frac{1}{2}};$$

N represents the number of electrocardiogram leads; and $x_i(t_k)$ represents the value of the $i^{th}$ lead in the N-lead set at time $t_k$.

16. The apparatus of claim 10, wherein the fractal index is defined by the equation $$K1=(PerimTot(t_k)\cdot FD(k))/SumArea(t_k)$$

wherein $t_k = k\delta t$ is the time after k intervals of time unit $\delta t$;

$$PerimTot(t_k) = \left(\sum_{i=1}^{N}x_i^2(t_k)\right)^{\frac{1}{2}} + LSUM(t_k)$$

$$LSUM(t_k) = LSUM(t_{k-1}) + \left(\sum_{i=1}^{N}(x_i(t_k) - x_i(t_{k-1}))^2\right)^{\frac{1}{2}};$$

$$FD(k)=\log(k)/(\log(k)+\log(DD(t_k)/LSUM(t_k)));$$

$$DD(t_k) = \max\left(\left(\sum_{i=1}^{N}x_i^2(t_k)\right)^{\frac{1}{2}}, DD(t_{k-1})\right);$$

$$SumArea(t_k) = SumArea(t_{k-1}) + \frac{1}{4}((D(t_k) + D(t_{k-1}) + L(t_k))(D(t_k) - D(t_{k-1}) + L(t_k))(-D(t_k) + D(t_{k-1}) + L(t_k))(D(t_k) + D(t_{k-1}) - L(t_k)))^{\frac{1}{2}};$$

where $D(t_k) = \left(\sum_{i=1}^{N}x_i^2(t_k)\right)^{\frac{1}{2}}$ and $$L(t_k) = \left(\sum_{i=1}^{N}(x_i(t_k) - x_i(t_{k-1}))^2\right)^{\frac{1}{2}};$$

N represents the number of electrocardiogram leads; and $x_i(t_k)$ represents the value of the $i^{th}$ lead in the N-lead set at time $t_k$.

17. The apparatus of claim 10, further comprising means for displaying the spatial loop.

18. The apparatus of claim 10, further comprising means for displaying the fractal index values and storing said fractal index values.

* * * * *